US005972691A

United States Patent [19]
Bates et al.

[11] Patent Number: 5,972,691
[45] Date of Patent: Oct. 26, 1999

[54] DEHALOGENATION OF POLYAMINE, NEUTRAL CURING WET STRENGTH RESINS

[75] Inventors: Robert Bates, Amersfoort, Netherlands; Harvey J. Branton, Sevenoaks, United Kingdom; David J. Hardman; Gary K. Robinson, both of Canterbury, United Kingdom

[73] Assignee: Hercules Incorporated, Wilmington, Del.

[21] Appl. No.: 08/482,398

[22] Filed: Jun. 7, 1995

[51] Int. Cl.$^6$ ............... D21C 3/00; C12N 1/00; C12N 1/20; D21F 11/00
[52] U.S. Cl. ............... 435/278; 435/29; 435/71.1; 435/822; 435/843; 435/849; 426/52; 162/5; 162/72; 162/157.1; 162/160; 162/161; 162/100; 162/156; 210/606; 523/400
[58] Field of Search ............... 162/157.1, 5, 72, 162/158, 160, 100, 161; 426/52; 435/278, 29, 822, 71.1, 843, 849; 424/93.1; 44/332; 523/400; 210/606

[56] References Cited

U.S. PATENT DOCUMENTS

| | | |
|---|---|---|
| 2,926,154 | 2/1960 | Keim . |
| 3,197,427 | 7/1965 | Schmalz . |
| 3,332,901 | 7/1967 | Keim . |
| 3,779,866 | 12/1973 | Azarowicz . |
| 3,891,589 | 6/1975 | Ray-Chaudhuri . |
| 4,240,935 | 12/1980 | Dumas . |
| 4,323,649 | 4/1982 | Higgins . |
| 4,447,541 | 5/1984 | Peterson . |
| 4,452,894 | 6/1984 | Olsen et al. . |
| 4,477,570 | 10/1984 | Colarnotolo et al. . |
| 4,490,471 | 12/1984 | Ghisalba et al. . |
| 4,493,895 | 1/1985 | Colarnotolo et al. . |
| 4,511,657 | 4/1985 | Colarnotolo et al. . |
| 4,535,061 | 8/1985 | Chakrabarty et al. . |
| 4,664,805 | 5/1987 | Focht . |
| 4,759,944 | 7/1988 | Fast et al. . |
| 4,761,376 | 8/1988 | Kulpa et al. . |
| 4,803,166 | 2/1989 | Kulpa et al. . |
| 4,804,629 | 2/1989 | Roy . |
| 4,806,482 | 2/1989 | Horowitz . |
| 4,816,403 | 3/1989 | Roy . |
| 4,833,086 | 5/1989 | Horowitz . |
| 4,853,334 | 8/1989 | Vandenbergh et al. . |
| 4,857,586 | 8/1989 | Bachem et al. . |
| 4,925,802 | 5/1990 | Nelson et al. . |
| 4,959,315 | 9/1990 | Nelson et al. . |
| 4,968,427 | 11/1990 | Glamser et al. . |
| 4,975,499 | 12/1990 | Bachen et al. . |
| 5,017,642 | 5/1991 | Hasegawa et al. . |
| 5,019,606 | 5/1991 | Marten et al. . |
| 5,024,949 | 6/1991 | Hegeman et al. . |
| 5,171,795 | 12/1992 | Miller et al. . |
| 5,256,727 | 10/1993 | Dulany et al. . |
| 5,330,619 | 7/1994 | Johnson et al. ............... 162/5 |
| 5,470,742 | 11/1995 | Bull et al. . |

FOREIGN PATENT DOCUMENTS

| | | |
|---|---|---|
| 02576 0 | 3/1988 | European Pat. Off. . |
| 0258666 | 3/1988 | European Pat. Off. . |
| 0258993 | 3/1988 | European Pat. Off. . |
| 0332967 | 9/1989 | European Pat. Off. . |
| 0349935 | 1/1990 | European Pat. Off. . |
| 0510987 | 10/1992 | European Pat. Off. . |
| 0510987 A1 | 10/1992 | European Pat. Off. . |
| 635048 | 11/1978 | U.S.S.R. . |
| 865727 | 4/1961 | United Kingdom . |
| 9222601 | 12/1992 | WIPO . |

OTHER PUBLICATIONS

Kasai et al., "Degradation of 2,3–Dichloro–1–propanol by a Pseudomonas sp.", *Agric. Biol. Chem.*, 54(12) (1990), pp. 3185–3190.

Wijngaard et al., "Degradation of Epichlorohydrin and Halohydrins by Bacterial Cultures Isolated from Freshwater Sediment", *Journal of General Microbiology*, 135 (1989), 2199–2208.

Wijngaard et al., "Purification and Characterization of Haloalcohol Dehalogenase from Arthrobacter sp. Strain AD2", *Journal of Bacteriology*, 173 (1991), pp.124–129.

Janssen et al., "Purification and Characterization of Bacterial Dehalogenase with Activity toward Halogenated Alkanes, Alcohols and Ethers", *Eur. J. Biochem.*, 171, (1988) pp. 67–72.

Castro et al., "Biological Cleavage of Carbon–Halogen Bonds Metabolism of 3–Bromopropanol by Pseudomonas sp.", *Biochimica et Biophysica Acta*, 100 (1965), pp. 384–392.

Ferguson et al., "Investigation of Anaerobic Removal and Degradation of Organic Chlorine from Kraft Bleaching Wastewaters", *Water Sci. Tech.*, 24, No. 3/4 (1991), pp. 241–250.

Janssen et al., "Hydrolytic and Oxidative Degradation of Chlorinated Aliphatic Compounds by Aerobic Microorganisms", *Advan. Appl. Biotechnol. Ser.* (1990), pp. 105–125.

Omori et al., "Bacterial Dehalogenation of Halogenated Alkanes and Fatty Acids", *Applied and Environmental Microbiology*, 35, No. 5 (1978), pp. 867–871.

Thayer, "Bioremediation: Innovative Technology for Cleaning Up Hazardous Waste", *Chemical and Engineering News* (Aug. 26, 1991), pp. 23–44.

(List continued on next page.)

Primary Examiner—Marian C. Knode
Assistant Examiner—Datquan Lee
Attorney, Agent, or Firm—Greenblum & Bernstein P.L.C.

[57] ABSTRACT

Process for making polyamine-epihalohydrin resin products having very low levels of epihalohydrin or epihalohydrin hydrolyzates, particularly useful in papermaking, which includes, amongst other features, producing a polyamine-epihalohydrin polymer in aqueous solution, terminating the reaction by cooling, adjusting the pH of the polyamine-epihalohydrin solution to from about 7.5 to about 11 and concurrently heating the solution to about 35 to about 50° C., and contacting the aqueous solution with selected microorganisms or an enzyme, and deactivating or removing the enzymes or microbes, cooling to about 20° C. and stabilizing the composition by adjusting the pH to about 2.0 to 5.0 by the addition of acid.

51 Claims, 1 Drawing Sheet

OTHER PUBLICATIONS

Frick, "Microbiological Cleanup of Groundwater Contaminated by Pentachlorophenol", p. 1, Omenn, *Environmental Biotechnology*, Plenum Press (1988).

Crawford et al., "Microbiological Removal of Pentachlorophenol from Soil Using a Flavobacterium", *Enzyme Microb. Technol.*, vol. 7 (Dec. 1985), p. 617.

"Biotrol Treatment Systems" brochure (date unknown) 4 pages.

EPA/540/5–88/003 (Nov. 1988), "The Superfund Innovative Technology Evaluation Program: Technoloy Profiles", pp. 13–16.

N. Dunlop–Jones, Paper Chemistry, Chapter 6: Wet–strength Chemistry, pp. 76–95, (1991).

M.H.J. Jacobs et al., Characterization of the epoxide hydrolase from an epichlorohydrin–degrading Pseudomonas sp., *European Journal of Biochemistry*, pp. 1–6 (Feb, 1991).

Hardman, D.J. and Slater, J.H. (1981) "Dehalogenases in Soil Bacteria", *J. Gen. Microbiol.*, 123, 117–128.

Jensen, H.L. (1960) "Decomposition of Chloroacetates and Chloropropionates by Bacteria", *Acta Agric. Scand.*, 10, 83–103.

Little, M. and Williams, P.A. (1971) "A Bacterial Halidohydrolase, Its Purification, Some Properties and Its Modification by Specific Amino Acids Reagents", *Eur. J. Biochem.*, 21, 99–109.

Senior, E. et al., (1976) "Enzyme Evolution in a Microbial Community Growing on the Herbicide Dalapon", *Nature*, 476–479.

Tonomura, K. et al. (1965) "Defluorination of Monofluoroacetate by Bacteria. Part I. Isolation of Bacteria and Their Activity of Defluorination", *Agric. Biol. Chem.*, 29, No. 2, pp. 124–128.

Slater, J.H. et al., (1979) "The Growth of *Pseudomonas putida* on Chlorinated Aliphatic Acids and Its Dehalogenase Activity", *J. Gen. Microbiol.*, 114, 125–136.

Weightman, A.J. et al., (1980) "Selection of *Pseudomonas putida* Strains with Elevated dehalogenase Activities by Continuous Culture Growth on Chlorinated Alkanoic Acids", *J. Gen. Microbiol.*, 121, 187–193.

European Search Report.

Taiwanese Office Action (translation).

Executed Verification of English Translation of Soviet Author's Certificate 635048.

Sallis, et al., Isolation and Characterization for Haloalkane Haledolydralase from *Rhodoccocus eltropolis* g2 J. Gen Micro. vol. 136, pp. 115–120 (1990).

FIG. 1

DEHALOGENATION OF POLYAMINE, NEUTRAL CURING WET STRENGTH RESINS

BACKGROUND OF THE INVENTION

1. Field of the Invention

The present invention relates to a process for making polyamine-epihalohydrin resin products having very low levels of residual epihalohydrin hydrolyzates with very high wet strength effectiveness.

2. Background and Material Information

Polyamine-epihalohydrin resins are cationic thermosetting materials used to increase the wet strength of papers. Often these materials contain large quantities of epihalohydrin hydrolysis products arising from the synthetic step (i.e., the reaction to produce the resin).

Commercial papermaking operations utilize paper wet strengthening formulations which comprise such cationic thermosetting polymers. In the papermaking process, waste material is frequently disposed of in landfills, etc. It is desirable to reduce the organohalogen content of such wastes to as low a level as possible. This waste is a substantially solid mass of material which is exposed to the environment. The exposure of the waste to the environment results in the selection of microorganisms which feed on the components in the waste. It is known that there are microorganisms which feed on the organohalogen compounds in the solid waste.

In the papermaking process the epichlorohydrin hydrolysis products arising from the synthetic step in the manufacture of polyamine-epichlorohydrin resins, are released into the environment in the water used to make paper, or into the air by evaporation during the paper drying step, or into the paper itself or a combination of these events. It is desirable to reduce and control these emissions into the environment to as low a level as possible.

Wet strength compositions which contain large quantities of epihalohydrin and/or epihalohydrin hydrolysis products display high wet strength effectiveness compared to similar products made using diminished or low quantities of epihalohydrin. Thus, there is a need to retain high wet strength effectiveness but also to reduce substantially the large quantities of undesirable halogenated by-products in the wet strength composition.

Several ways of reducing the quantities of epihalohydrin hydrolysis products have been devised. Reduction in the quantity of epihalohydrin used in the synthetic step is an alternative taught in U.S. Pat. No. 5,171,795. A longer reaction time results. Control over the manufacturing process is taught in U.S. Pat. No. 5,017,642 to yield compositions of reduced concentration of hydrolysis products.

Reduction in the amount of epihalohydrin used is effective in reducing epihalohydrin and epihalohydrin hydrolysis products in the wet strength composition but has the undesirable side effect of reducing wet strength performance in proportion to the reduction in epihalohydrin used. Therefore, conventional wisdom dictates that reduction in the amount of epihalohydrin employed in the polymerization reaction is to be avoided or else high wet strength effectiveness of such resins will be sacrificed.

Post-synthetic treatments may be used. U.S. Pat. No. 5,256,727 teaches that reacting the epihalohydrin and its hydrolysis products with dibasic phosphate salts or alkanolamines in equimolar proportions converts the chlorinated organic compounds into non-chlorinated species. To do this it is necessary to conduct a second reaction step for at least 3 hours, which adds significantly to costs and generates quantities of unwanted organic materials in the wet strength composition. In compositions containing large amounts of epihalohydrin and epihalohydrin hydrolysis products (e.g., about 1–6% by weight of the composition), the amount of organic material formed is likewise present in undesirably large amounts.

WO 92/22601 teaches that halogenated by-products can be removed from products containing high levels of halogenated by-products as well as low levels of halogenated by-products by the use of ion exchange resins. However, it is clear from the data presented that there are significant yield losses in wet strength composition and a reduction in wet strength effectiveness.

It is known that nitrogen-free organohalogen-containing compounds can be converted to a relatively harmless substance. For example, 1,3-dichloro-2-propanol, 1-chloro-2,3-propanediol, and epichlorohydrin have been treated with alkali to produce glycerol.

The conversion of nitrogen-free organohalogen compounds with microorganisms containing a dehalogenase is also known. For example, C. E. Castro, et al. ("Biological Cleavage of Carbon-Halogen Bonds Metabolism of 3-Bromopropanol by Pseudomonas sp.", *Biochimica et Biophysica Acta*, 100, 384–392, 1965) describe the use of Pseudomonas sp. isolated from soil that metabolizes 3-bromopropanol in sequence to 3-bromopropionic acid, 3-hydroxypropionic acid and $CO_2$.

Various U.S. Patents also describe the use of microorganisms for dehalogenating halohydrins, e.g., U.S. Pat. Nos. 4,452,894; 4,477,570; and 4,493,895. Each of these patents is hereby incorporated by reference as though set forth in full herein.

EP-A-0 510 987 A1 teaches the use of microorganisms or enzymes derived from microorganisms to remove epihalohydrin and epihalohydrin hydrolysis products from wet strength compositions without reduction in wet strength effectiveness. Processes of removal are described which remove up to 2.6 weight per cent of halogenated by-product based on the weight of the composition. The amount of microorganism or enzyme used is in direct proportion to the quantity of halogenated by-product present. Thus, when present in large quantities (e.g., more than about 1% by weight of the composition) a large proportion of microorganism or enzyme is needed to adequately remove the unwanted product. Large quantities of halogenated byproduct can be toxic to the microbes employed in such dehalogenation processes. EP-A-0 510 987 A1 is a family member of U.S. patent application Ser. No. 08/243,492, filed May 16, 1994, now U.S. Pat. No. 5,470,742 which is both a continuation of U.S. patent application Ser. No. 07/866,216, filed Nov. 9, 1992, and a continuation-in-part of U.S. patent application Ser. No. 07/690,765, filed Apr. 9, 1992. Each of these documents is hereby incorporated by reference as though set forth in full herein.

It is also known that epihalohydrin and epihalohydrin hydrolyzates can be reacted with bases to form chloride ion and polyhydric alcohols. U.S. Pat. No. 4,975,499 teaches the use of bases during the synthetic step to reduce organo chlorine contents of wet strength composition to moderate levels (e.g., to moderate levels of from about 0.11 to about 0.16%) based on the weight of the composition. U.S. Pat. No. 5,019,606 teaches reacting wet strength compositions with an organic or inorganic base.

Each of the foregoing approaches has provided less than optimal results, and there has been a continuing need for improvement.

SUMMARY OF THE INVENTION

The invention relates to the discovery that the treatment of wet strength compositions with an inorganic base after the synthetic step (i.e., after the polymerization reaction to form the resin) has been completed and the resin has been stabilized at low pH, similarly reduces the organo halogen content of wet strength compositions (e.g., chlorinated hydrolysis products) to moderate levels (e.g., about 0.5% based on the weight of the composition). Surprisingly, the stability of the wet strength composition is not impaired, provided the molar ratio of epihalohydrin to secondary amine in the polyamine is greater than unity. The composition so formed can then be treated with microorganisms or enzymes to economically produce wet strength compositions with very low levels of epihalohydrins and epihalohydrin hydrolysis products. Additionally, the wet strength effectiveness of these compositions is identical to that of the starting material, and the stability of the composition is likewise unimpaired.

An object of the invention is to provide a process for making wet strength compositions starting from high levels of reacted epihalohydrin that are stable to prolonged storage and have high levels of wet strength effectiveness substantially identical to that of the starting material, i.e., the resin prior to treatment by the process of the invention.

It is also an object of the invention to provide a process for making wet strength compositions with low or very low concentrations of epihalohydrin or epihalohydrin hydrolysis products.

The process comprises:
a) producing a polyamine-epihalohydrin polymer in aqueous solution by reacting epihalohydrin in molar excess relative to the secondary amine functionality in the polyamine prepolymer;
b) concurrently heating and adjusting the pH of the polyamine-epihalohydrin solution to a pH range and temperature range effective to liberate halide ions from epihalohydrins and/or epihalohydrin hydrolyzates resulting from the reaction of step a) to the solution, and maintaining these conditions for about 5 to about 50 minutes; and
c) contacting the aqueous solution resulting from step b) with microorganisms, or an enzyme isolated from such microorganism, in an amount, and at a pH and temperature effective to dehalogenate residual quantities of organically bound halogen.

Preferably, step a) is conducted in aqueous solution such that the epihalohydrin used to make the polymer is in molar excess relative to the secondary amine functionality in the polymer. Further the reaction is preferably terminated at the required molecular weight (determined by measuring the viscosity of the polymer), preferably by cooling and, optionally, adjusting the pH to less than about 8.0.

Additionally, preferably, step b) further comprises adjusting the pH of the polyamine-epihalohydrin solution to a range of from about 7.5 to about 11 and concurrently heating the solution to a range of from about 35 to about 50° C., and maintaining such conditions for about 5 to about 50 minutes.

Step c) is preferably conducted by contacting the aqueous solution resulting from the pH treatment of step b) with selected microorganisms at a cell concentration of greater than about $5 \times 10^7$ cells/ml, or an enzyme, at a pH in the range of from about 4 to about 8 and a temperature range of about 25 to about 35° C. for a period of time from about 6 to about 50 hours duration.

Also preferably, the process further comprises an additional step, d), which comprises deactivating or removing the enzymes or microbes, cooling to about 20° C. and stabilizing the composition by adjusting the pH to a range of about 2.0 to about 5.0 by the addition of acid.

In another aspect of the invention, the invention provides a process for making an additive for imparting improved wet strength to paper, the additive comprising polyamine-epihalohydrin resin product having very low levels of epihalohydrin or epihalohydrin hydrolozates, the process comprising:
a) producing a polyamine-epihalohydrin polymer by reacting a polyamine selected from a polyalkylene amine of the general formula $$H_2N((CH_2)_mNH)_n(CH_2)_mNH_2$$

where n is an integer from about 1 to about 6 and m is an integer from about 2 to about 8; or, a polyamidoamine of the general formula $$\{CO(CH_2)_yCONH(CH_2)_m(NH(CH_2)_m)_nNH\}$$

where y is an integer from about 3 to about 5 and m and n have the same value as given above, with an epichlorohydrin in aqueous solution such that the epichlorohydrin used to make the polymer is in molar excess relative to the secondary amine functionality in the polymer, and terminating the reaction, by cooling and, optionally, adjusting the pH to less than about 8.0;
b) adjusting the pH of the polyamine-epichlorohydrin solution to a range of from about 9.5 to about 10.5 and concurrently heating the solution to a range of from about 35 to about 50° C., and maintaining such conditions for about 5 to about 50 minutes;
c) contacting the aqueous solution resulting from the pH treatment of step b) with microorganisms selected from the group consisting of *Arthrobacter histidinolovorans, Arthrobacter erithii, Agrobacterium tumefaciens, Rhodococcus dehalogenans, Pseudomonas cepacia*, and mixtures thereof, at a cell concentration of greater than about $10^7$ cells/ml, or an enzyme, at a pH in the range of from about 4 to about 8 and a temperature range of about 25 to about 35° C. for a period of time from about 6 to about 50 hours duration; and
d) deactivating or removing the enzymes or microbes, cooling to about 20° C. and stabilizing the composition by adjusting the pH to a range of about 2.0 to about 5.0 by the addition of acid.

The resulting product has concentrations of epihalohydrin and epihalohydrin hydrolysis products of less than about 1000 ppm total based on the as-received weight of the composition and preferably less than about 100 ppm, more preferably less than about 10 ppm and most preferably less than about 5 ppm. This compares to starting concentrations of 10000 ppm or more.

Since the present invention is especially useful for the production of a paper wet strengthening formulation, the present invention further encompasses a method of making paper. The method of making paper comprises the steps of:
a) providing a wet strength composition produced as defined above; and
b) adding the paper wet strengthening formulation to a stream in a papermaking process.

The processes of the invention can be carried out batchwise or continuously, and this applies to the biodehalogenation methods as well as the papermaking methods of the invention.

The methods of the invention may also be carried out in intermittent fashion, in which event the method is termed a "semi-continuous" method. In the semi-continuous method, the reactor may be run, for example, for an 8 to 16 hour period, followed by being operated batchwise for the remainder of the day. The semi-continuous method involves the criticalities of both the continuous method and the batch method.

The effectiveness of the process of the invention is surprising, because the combination of steps employed in the invention would be expected, when conducted serially or sequentially, to produce compositions wherein the wet strength effectiveness has been compromised. In contradistinction, the process of the invention can be conducted and produce wet strength compositions which have low epihalohydrin or epihalohydrin hydrolysis products, without sacrificing wet strength effectiveness.

DETAILED DESCRIPTION OF PREFERRED EMBODIMENTS OF THE INVENTION

The invention involves contacting polyamine-epihalohydrin resin products containing unreacted epihalohydrin and epihalohydrin hydrolyzates with an inorganic base under controlled pH and temperature to effect a reduction of concentration of the unreacted epihalohydrin and epihalohydrin hydrolyzates with the liberation of chloride ion and glycerol and without denaturing or destabilizing the polyamine-epihalohydrin solution.

It has unexpectedly been found that 3-chloro-1,2-propanediol (also referred to herein as "CPD") is the major dehalogenation product resulting from base treatment of unreacted epihalohydrin and epihalohydrin hydrolyzates. Since CPD is non toxic to the microbes employed in the invention, the materials resulting from the base treatment step can subsequently be efficaciously treated with microorganisms capable of dehalogenating epihalohydrin and epihalohydrin hydrolozates. The alkali treatment reduces the DCP (1,3-dichloropropanol) concentration to non-toxic levels and generates glycerol which is then utilized along with the remaining epihalohydrin hydrolysis products to generate biomass.

Low levels of epihalohydrin or epihalohydrin hydrolyzates obtained by the process of the invention are on the order of 1000 ppm or less, preferably 100 ppm or less, preferably 10 ppm, or less, and most preferably 5 ppm or less.

It is important to note that polyamine-epihalohydrin resins in which the ratio of epihalohydrin to secondary amine is less than unity are destabilized by this process. Thus, submolar ratio derived polymers are unsuitable feedstreams for this process. Although there is no upper limit with regard to the ratio of epihalohydrin to secondary amine, an economic limit is about 3.5:1, preferably less than about 1.9:1, and more preferably less than about 1.5:1.

Suitable average molecular weights (Mw) for polyamine-epihalohydrin polymer are in the range of from about 200,000 to about 450,000, and preferably from about 300,000 to about 450,000, and most preferably from about 375,000 to about 450,000. Molecular weight is preferably determined using gel permeation chromatography (also referred to as size exclusion chromatography) using a refractive index detector.

A preferred group of polymers for use in the present invention includes cationic polymers, alone or together with other polymers used for the purpose of imparting wet strength to paper. A listing of many polymers useful in papermaking wet strengthening formulations is described in *Paper Chemistry*, ISBN 0-216-92909-1, pages 78–96, published in the U.S.A. by Chapman Hall, New York. Chapter 6 of this book is entitled "Wet Strength Chemistry", and is hereby incorporated by reference, as though set forth in full herein. Chapter 6 describes several classes of polymers which are used to impart wet strength to paper, including: polyaminoamide-epichlorohydrin resin, urea-formaldehyde resin, melamine-formaldehyde resin, epoxidized polyamide resin, glyoxalated polyacrylamide resin, polyethyleneimine resin, dialdehyde starch, proteinaceous adhesive treated with formaldehyde, cellulose xanthate (viscose), synthetic latex, vegetable gum, glyoxal, epichlorohydrin resin. The polyaminoamide-epichlorohydrin resin may be a Kymene® brand polyaminoamide-epichlorohydrin resin, such as Kymene® 517, Kymene® 2064, Kymene® 450, Kymene® 367 and Kymene® 557H resins.

The polymers resulting from the reaction step (i.e. step a)) include cationic polymers such as polyaminoamide-epichlorohydrin resins, which may be used alone or in combination with the other polymers used for the wet strengthening of paper. Preferred resins for the purposes of this invention include polyaminoamide-epichlorohydrin wet-strength resins as described in U.S. Pat. Nos. 2,926,154; 3,332,901; 3,891,589; 3,197,427; 4,240,935; 4,857,586; European Patent Publication 0,349,935, and Great Britain Patent 865,727. Processes for making these known resins are also disclosed in these documents, which are hereby incorporated reference as though set forth in full herein.

The limits of pH treatment represent a balance between the required short time for completion and the degradative effect of strong alkali on the polymer and consequent loss in wet strength performance. The preferred treatment range is from about pH 7.5 to about pH 11, more preferably a pH range of from about 8.0 to about 10.5 and most preferably a pH range of about 9.5 to about 10.5.

Likewise, the speed of reaction is influenced by temperature of the reaction system. Excessively high temperatures present a risk of uncontrolled crosslinking of the product. Low temperatures can result in excessively long reaction times, also with a minor risk of crosslinking of the product. The preferred temperature range is from about 25° C. to about 50° C., more preferably from about 35° C. to about 50° C. and most preferably from about 45° C. to about 50° C.

This part of the process is well suited as an auxiliary step in the conventional synthesis of polyamine-epihalohydrin resins.

The type of polyamine resin contemplated by this invention is either:

a polyalkylene amine of the general formula

$$H_2N((CH_2)_mNH)_n(CH_2)_mNH_2$$

where n is an integer from about 1 to about 6, and m is an integer from about 2 to about 8 or a polyamidoamine of the general formula $$\{CO(CH_2)_yCONH(CH_2)_m(NH(CH_2)_m)_nNH\}$$

where y is an integer from about 3 to about 5 and m and n have the same value above.

Epihalohydrins have the general formula where x is an integer from about 1 to about 3 and X is chlorine, bromine or iodine.

Of the epihalohydrins, epichlorohydrin is much preferred where X is chlorine, and x is 1.

The foregoing polyamines and epihalohydrins are readily available, and those of ordinary skill in the art can readily select the appropriate polyamine and epihalohydrin for use in the present invention.

Epihalohydrin hydrolyzates comprise mono- and di-halo-substituted polyhydric alcohols derived from nucleophilic attack by either halide ion or hydroxide ion on the precursor molecule. In the case of epihalohydrin, the three most abundant hydrolysis products present are 1,3-dichloro-2-propanol, 3-chloro-1,2-propanediol and 2,3-dichloro-1-propanol.

The concentration of epihalohydrins in the wet strength composition immediately prior to treatment is in the range of from about 300 to about 1000 ppm, the concentration of dihaloalcohol is in the range of from about 10000 ppm to about 20000 ppm, and the concentration of mono-haloalcohol is in the range of from about 3000 ppm to about 5000 ppm.

The precise concentration of these materials is not materially essential to the process since the process, by adjustment, will treat wet strength compositions with widely differing concentrations of hydrolyzates. This flexibility is especially valuable commercially in coping with batch-to-batch or product-to-product variation. Optimization can be readily accomplished by those of ordinary skill in the art.

Suitable inorganic bases can be readily selected by those of ordinary skill in the art, such as, sodium hydroxide and potassium hydroxide, which are preferred, especially for their low cost and convenience. Other suitable bases include sodium carbonate, potassium carbonate, aqueous ammonia, sodium phosphate and potassium phosphate ($M_3PO_4$).

Following the inorganic base treatment step, the wet strength composition may be fed to a second reactor containing a microorganism or enzyme in adequate quantities to process the remaining epihalohydrin hydrolyzates to very low levels. Alternatively, the treatment with the microorganism or enzyme can be conducted in the same reactor as the inorganic base treatment step. If the same reactor is employed in dehalogenation, the pH excursion resulting from the base treatment step must be achieved prior to inoculation of the product with the microorganism. Microorganisms use dehalogenase enzymes to liberate halide ion from the epihalohydrin and haloalcohol and then use further enzymes to break down the reaction products ultimately to carbon dioxide and water. In the case of 1,3-dichloropropanol ("DCP"):

Exemplary microorganisms which contain dehalogenating enzymes capable of dehalogenating haloalcohols and epihalohydrins have been found in the following species:

| NAME | NCIMB[1] DEPOSIT IDENTITY |
|---|---|
| Arthrobacter histidinolovorans | 40274 |
| Arthrobacter erithii | 40271 |
| Agrobacterium tumefaciens | 40272 |
| Rhodococcus dehalogenans | 40383 |
| Pseudoinonas cepacia | 40273 |

[1]NCIMB, located at 23 St. Machar Drive, Aberdeen AB2 1RY, Scotland, UK stands for "National Collection of Industrial and Marine Bacteria". NCIMB is an organization in the United Kingdom responsible for documenting and retaining samples of bacteria submitted for patent application purposes.In patent matters, NCIMB will supply to interested parties who so request, authentic samples of bacteria claimed in patent literature.

Mixtures of the foregoing can also be employed. Several strains of microorganisms from these species have been found to generate enzymes suitable for the process. NCIMB 40271, 40272, 40273 and 40274 were deposited on Apr. 4, 1990. NCIMB 40383 was deposited on Mar. 11, 1991.

Such microorganisms are conventional. Such microorganisms are obtainable by batch or continuous enrichment culture. Inoculation of enrichment isolation media with soil samples taken from organohalogen-contaminated soil results in mixed microbial communities, which can be sub-cultured, in a plurality of subculturing steps (preferably 2 to 5 subculturing steps), using increasing concentrations of the particular organohalogen-containing compound for which selection is sought.

The microorganisms containing suitable enzymes are suitably used to dehalogenate the epihalohydrin hydrolyzates contained in the wet strength composition following inorganic base treatment. The enzymes and microorganisms are maintained in a suitable concentration to substantially metabolize the hydrolyzates to chloride ion and ultimately carbon dioxide and water. Thus the concentration of hydrolyzates in the wet strength composition after treatment is preferably less than about 100 ppm (parts per million by weight relative to the total weight of aqueous solution containing wet strength resins after the bioreaction step), more preferably less than about 10 ppm (parts per million by weight relative to the total weight of aqueous solution containing wet strength resins after the bioreaction step), and most preferably less than about 5 ppm (parts per million by weight relative to the total weight of aqueous solution containing wet strength resins after the bioreaction step).

To achieve this, the concentration of microorganisms should be at least about $5 \times 10^7$ cells/ml, preferably at least about $10^8$ cells/ml and most preferably at least about $10^9$ cells/ml. To maintain optimum active content of cells in the reactor, the reaction is best carried out at about 30° C. ±5 in the presence of oxygen (e.g., from about 5 to about 100% DOT) and nutrients in a stirred tank reactor. As used herein, the term "DOT" refers to "dissolved oxygen tension" and is the amount of oxygen, expressed as a percentage, dissolved in a given volume of water relative to oxygen-saturated water at the same temperature and pressure. The residence time is controlled by flow rate and monitored to ensure complete reaction. Thus, at steady state the concentration of epihalohydrin hydrolyzates in the reactor will be from about 1 to about 1000 ppm.

The present invention also involves the reaction of an enzyme with the organohalogen compound, whereby the organohalogen is dehalogenated. As used herein, the term "enzyme" refers to any dehalogenase, i.e. any enzyme capable of dehalogenating a nitrogen-free organohalogen compound. Preferably, the enzyme is obtained from a living cell, which is thereafter used for the dehalogenation of nitrogen-free organohalogen compounds. Suitable enzymes include those produced by the microorganisms identified above.

Although the precise identity of the enzymes of the method has not been determined, the enzymes which effectuate the method belong to the class of enzymes variously termed "haloalcohol dehalogenases" or "hydrogen halide lyase type dehalogenases" or "halohydrin hydrogen-halide lyases".

Thus, for dehalogenation, the invention contemplates the use of either living cells or an immobilized, unrefined cell-free extract or refined dehalogenase. The term "biodehalogenation" refers to the dehalogenation of an organohalogen compound using such materials.

In general, if an enzyme is employed, the enzyme may be added to the composition in an amount of from about $2.5 \times 10^{-6}$ to $1 \times 10^{-4}$ weight percent, based on the weight of the composition. However, the enzyme is preferably added to the composition in an amount of from about $2.5 \times 10^{-5}$ to $0.75 \times 10^{-4}$ weight percent, most preferably in an amount of from about $4 \times 10^{-5}$ to $6 \times 10^{-5}$ weight percent, based on the weight of the composition.

Suitable biocatalysts can also be employed. Such biocatalysts can be readily selected by those of ordinary skill in the art. *Agrobacterium tumefaciens* HK7 (NCIMB 40313) represents another biocatalyst for use in the method of the present invention. The most preferred biocatalyst for use in the method of the present invention is a two-component mixture of *Agrobacterium tumefaciens* and *Arthrobacter histidinolovorans* NCIMB 40313 was deposited on Aug. 31, 1990. Although the precise identity of the enzymes which make the method operable has not been made, it is believed that the enzymes which effectuate the method belong to the class of enzymes termed "hydrogen halide lyase type dehalogenase".

The method of biodehalogenation in accordance with the present invention is carried out by contacting a microorganism or cell-free enzyme-containing extract with the aqueous composition containing the unwanted organohalogen contaminants. Such contact is typically achieved by forming a slurry or suspension of the microorganism or cell-free extract in the aqueous composition, with sufficient stirring.

If desired, the microorganism or enzymes can be removed from the product stream by filtration, sedimentation, centrifugation or other means known to those skilled in the art. Alternatively the microorganisms or enzymes can remain in the final product and optionally deactivated by thermal sterilization (e.g., by treatment at 140° C. for 20 seconds) or by the addition of a suitable concentration of a suitable biocidal agent. Suitable biocidal agents can be readily selected by those of ordinary skill in the art. Thus, deactivation of the microorganism can be performed by reducing the pH of the aqueous mixture to 2.8, then adding a proprietary biocidal agent (e.g. Proxell® BD biocidal agent, which comprises 1,2-benzisothiazolin-3-one) in sufficient quantity, normally 0.02% to 0.1%, based on the weight of the aqueous composition. The biocidal agent may be added along with potassium sorbate.

The removal of the microorganism may be performed by one or more of the steps of filtration, centrifugation, sedimentation, or any other known techniques for removing microbes from a mixture. The microorganisms mineralize the nitrogen free organohalogen compounds, producing $CO_2$, water, and biomass, with no glycerol left in the resin. Where the biocatalyst is an immobilized dehalogenase, the product of the reaction is glycidol.

A problem associated with the removal of the microbes from the mixture is that intensive methods of separation such as microfiltration remove not only microbes but also particles of cationic polymer, with the result that the wet strength properties are reduced, which is undesirable. Therefore it is preferable to leave the deactivated microorganism in the mixture to avoid the problem of reducing wet strength properties.

The composition is stabilized by adjusting the pH to a range of from about 2.0 to about 5.0 by the addition of a suitable acid. Preferred acids are mineral acids (inorganic acids) and include hydrochloric acid, sulphuric acid, phosphoric acid. Hydrochloric acid is preferred, especially for its low cost and convenience.

The final product of the process is a composition suitable as a paper wet strength formulation. The paper made from such a composition will contain essentially no detectable levels of epihalohydrin hydrolyzates nor will the air and aqueous effluents from the paper making process used to make paper using this wet strengthening composition.

Those of ordinary skill in the paper making art will readily understand how to employ the wet strength resins of the invention. The resins of the invention are employed in the same way as other conventional wet strength polyamine-epihalohydrin resins. Such uses are described in *Paper Chemistry*, ISBN 0-216-92909-1, published in the U.S.A. by Chapman Hall, New York (cited above), which is hereby incorporated by reference as though set forth in full herein.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Inorganic Base Treatment of Wet Strength Formulation to Reduce 1,3-dichloro-2-propanol Concentration From 10000 ppm Based On the Dry Weight of Polyamidoamine-epihalohydrin Resin One batch of Kymene 557H containing 10000 ppm of 1,3-dichloro-2-propanol was split into two parts and maintained at 50° C. The pH was adjusted to two values (one for each batch) and maintained at constant pH value by continuous addition of 50% sodium hydroxide.

| Time (min) | % Chloride ion released |
|---|---|
| pH 8.5 | |
| 0 | 0 |
| 10 | 66.9 |
| 20 | 49.6 |
| 30 | 77.8 |
| 68 | 82.4 |
| pH 9.5 | |
| 0 | 0 |
| 11 | 90.5 |
| 30 | 92.7 |
| 55 | 93.6 |

EXAMPLE 2

Biodehalogenation of Inorganic Base Treated Wet strength Formulation

The product resulting from treating Kymene 557H at pH 9.5 for 11 minutes at 50° C. was neutralized to pH 5.8 and transferred to a stirred tank reactor at 30° C. A blend of microorganisms comprising an inoculum representing 10% volume of Kymene to be treated was added. This represents a starting value of cell concentration of from about $10^5$ to about $10^6$ cells/ml. This starting value corresponds to a final treatment level of about $10^9$ cells/ml as the process proceeds. The inoculum was added, together with trace quantities of urea, potassium dihydrogen phosphate, disodium hydrogen phosphate and magnesium sulphate as nutrients.

The microorganisms used had the following composition:

*Arthrobacter histidinolovorans* HK1 excess

*Agrobacterium tumefaciens* HK7

After 6–8 hours the total concentration of 1,3-dichloro-2-propanol and 3-chloro-1,2-propanediol was reduced to below 5 ppm based on the weight of the wet strength composition.

The concentration of epi hydrolyzates was measured by extracting the analytes from a sample of the product and measuring the concentration of analyte in the extract by gas chromatography using controls of known concentrations and then relating the measured concentration to the original weight of the sample of the product.

In continuous processes, the culture added as exemplified above will continue to grow and replace those cells leaving the reactor, thus reaching a steady state of about $10^9$ cells/ml.

EXAMPLE 3

Wet Strength Effectiveness of Alkali/biotreated Kymene 557H

The product resulting from Example 2 was used to wet strengthen paper (50/50 bleached birch and pine). The wet strength was measured in comparison with the untreated Kymene 557H starting material.

The dry strength and wet strength of the wet strengthened paper was measured according to TAPPI (Technical Association of the Pulp and Pater Industry), method T-494-OM-88. As used herein "dry" paper refers to paper of 5–10% moisture content, "wet" paper refers. to paper soaked in water for 2 hours at 20° C., and then tested while still wet.

| Sample | Addition level % db | Off machine test results | | | Oven cured (80% 30 min) wet strength | | | Naturally aged wet strength | | |
|---|---|---|---|---|---|---|---|---|---|---|
| | | dry | wet | wet/dry % | dry | wet | wet/dry % | wet | dry | wet/dry % |
| Example 2 | 0.25 | 3.28 | 0.23 | 7.30 | 3.25 | 0.43 | 14.08 | 3.72 | 0.35 | 10.14 |
| | 0.50 | 3.49 | 0.33 | 10.14 | 3.56 | 0.56 | 16.18 | 3.70 | 0.47 | 13.61 |
| | 1.0 | 3.55 | 0.45 | 13.53 | 3.80 | 0.73 | 20.49 | 3.78 | 0.58 | 16.37 |
| Kymene 557H | 0.25 | 3.48 | 0.29 | 8.33 | 3.39 | 0.47 | 13.86 | 3.39 | 0.39 | 11.50 |
| | 0.0 | 3.39 | 0.36 | 10.62 | 3.44 | 057 | 16.57 | 3.59 | 0.50 | 13.93 |
| | 1.0 | 3.50 | 0.48 | 13.71 | 3.67 | 0.69 | 18.80 | 3.57 | 0.59 | 16.53 |

These results show that, within experimental error, the wet strength effectiveness of the two compositions is the same.

In Example 3, the addition level refers to the amount of active polymer added to the paper on a dry basis. The sample prepared in Example 2 contains mineral salts from the successive additions of acid and alkali and biomass from the bioreactor, none of which contribute to wet strength nor are present in the starting material Kymene 557H. The addition to paper of the resin from Example 2 is made on an equal dry active basis to that of Kymene 557H, thus is on a total dry matter basis 7% high, the extra addition of dry matter comprising inactive salts, biocide and biomass. Thus, for the resin in Example 2:

| Dry active basis (weight) | Total dry matter basis (weight) |
|---|---|
| 0.25% | 0.2675% |
| 0.50% | 0.535% |
| 0.75% | 0.802% |

The dry and wet strength test results are in the units: Kilo Newtons/meter. As used herein, "naturally aged" refers to paper samples aged 7 days at 23° C. and 50% relative humidity, prior to testing.

EXAMPLE 4

Illustration of Continuous Process of the Invention

Figure 1:
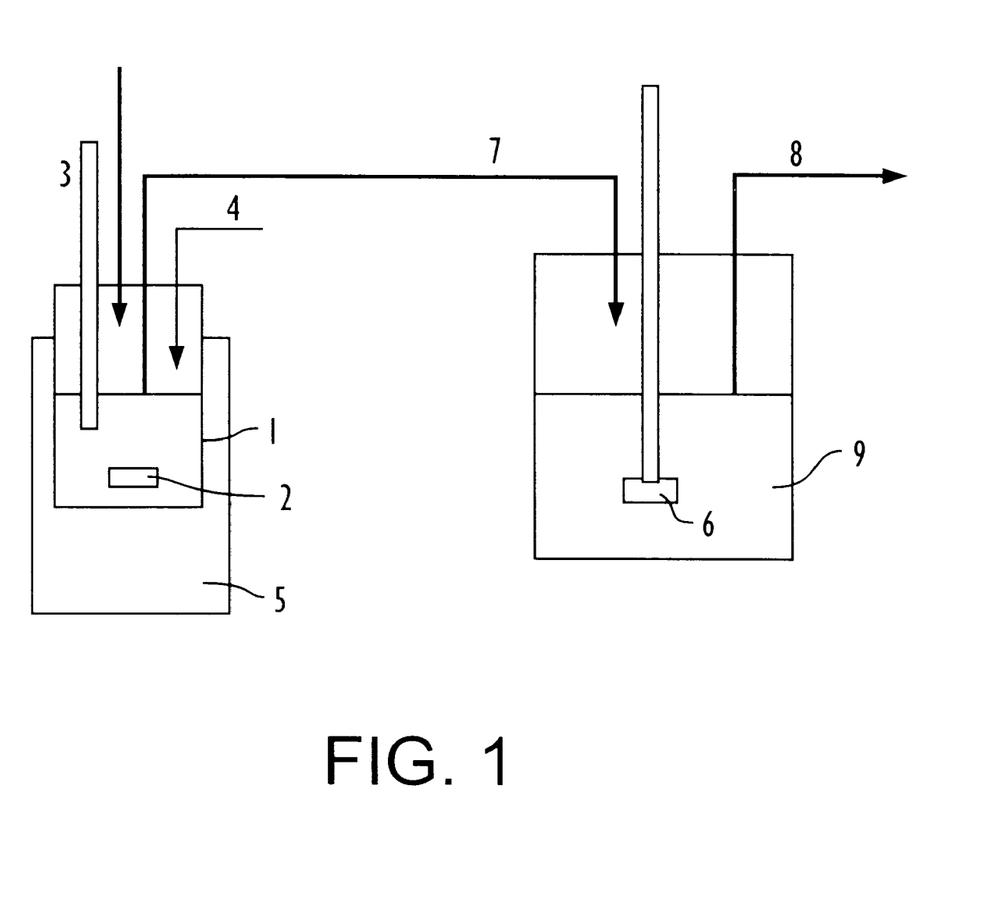
FIG. 1 is a schematic representation of a process according to the invention, carried out continuously.

In continuous process aspects of the invention, such as is shown schematically in FIG. 1, the wet strength composition containing high levels of hydrolysis products is added continuously under flow control to a small stirred reactor 1 maintained at constant temperature of 50° C., as by a water bath 5 maintained at 50° C., provided with suitable stirring means 2. The reactor is also maintained at constant pH of 10.0 by continuous controlled addition of inorganic base, as at addition point 4. The flow rate and reactor level are adjusted to maintain a residence time of 15.9 minutes. Effluent 7 from the small reactor is fed to a larger reactor 9 under pH, temperature, and flow control to give a residence time in the larger reactor of 9.6 hours. The larger reactor, also provided with suitable stirring means 6, contains microbes or enzymes in suitable concentration to degrade rapidly and to a sufficient extent the remaining concentrations of epihalohydrin hydrolyzates.

The effluent 8 from the larger reactor is removed and further adjusted for pH, viscosity and active content batchwise or continuously to final product specification.

Further post treatment operations can include removal or inactivation of the microorganisms, enzymes and/or biocatalyst, as set forth above.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for making polyamine-epihalohydrin resin, comprising:
   a) producing polyamine-epihalohydrin resin in aqueous solution by reacting epihalohydrin with polyamine prepolymer, said epihalohydrin being in molar excess relative to secondary amine functionality in the polyamine prepolymer;
   b) concurrently heating and adjusting the pH of the polyamine-epihalohydrin resin in aqueous solution to a pH range of about 7.5 to 11 and temperature range effective to liberate halide ions from at least one of epihalohydrins and epihalohydrin hydrolyzates to solution, and maintaining said pH and said temperature for at least 5 minutes; and
   c) contacting the aqueous solution resulting from b) with at least one microorganism, or at least one enzyme isolated from said at least one microorganism, in an amount, and at a pH and temperature effective to dehalogenate residual quantities of organically bound halogen.

2. The process of claim 1, wherein said polyamine-epihalohydrin resin is prepared by reacting epihalohydrin and at least one member selected from the group consisting of
   polyalkylene amine of the general formula where n is an integer from about 1 to about 6 and m is an integer from about 2 to about 8; and
   polyamidoamine of the general formula where y is an integer from about 3 to about 5 and m and n have the same value as given above.

3. The process of claim 1, wherein said epihalohydrin is epichlorohydrin.

4. The process of claim 1, wherein a) is conducted under conditions wherein the ratio of epihalohydrin to secondary amine functionality is less than 3.5:1.

5. The process of claim 4, wherein a) is conducted under conditions wherein the ratio of epihalohydrin to secondary amine functionality is less than 1.9:1.

6. The process of claim 5, wherein a) is conducted under conditions wherein the ratio of epihalohydrin to secondary amine functionality is less than 1.5:1.

7. The process of claim 1, further comprising terminating the reaction of a) by cooling.

8. The process of claim 7, wherein said cooling is followed by adjusting the pH of said aqueous solution to less than 8.0.

9. The process of claim 1, wherein the pH range of b) is from about 7.5 to about 11 and a temperature in the range of from about 25° C to about 50° C.

10. The process of claim 9, wherein said pH range of b) is in the range of from about 8.0 to about 10.5 and a temperature in the range of from about 35° C. to about 50° C.

11. The process of claim 10, wherein said pH range of b) is in the range of from about 9.5 to about 10.5 and a temperature in the range of from about 45° C. to about 50° C.

12. The process of claim 1, wherein c) is conducted at a pH range of from about 4 to about 8 and a temperature range of about 25 to about 35° C.

13. The process of claim 1, wherein c) is conducted in the presence of a microorganism selected from the group consisting of *Arthrobacter histidinolovorans* NCIMB Registry No. 40274; *Arthrobacter erithii* NCIMB Registry No. 40271; *Agrobacterium tumefaciens* NCIMB Registry No. 40272; *Rhodococcus dehalogenans* NCIMB Registry No. 40383; *Pseudomonas cepacia* NCIMB Registry No. 40273, and mixtures thereof.

14. The process of claim 1, wherein c) is conducted in the presence of a microorganism selected from the group consisting of *Arthrobacter histidinolovorans* HK1 and *Agrobacterium tumefaciens* HK7, and mixtures thereof.

15. The process of claim 14, wherein c) is conducted in the presence of a mixture comprising an excess of *Arthrobacter histidinolovorans* HK1 and *Agrobacterium tumefaciens* HK7.

16. The process of claim 1, wherein the aqueous solution resulting from c) has a concentration of epihalohydrin and epihalohydrin hydrolysis products of less than 1000 ppm.

17. The process of claim 1, wherein the aqueous solution resulting from c) has a concentration of epihalohydrin and epihalohydrin hydrolysis products of less than 100 ppm.

18. The process of claim 1, wherein the aqueous solution resulting from c) has a concentration of epihalohydrin and epihalohydrin hydrolysis products of less than 10 ppm.

19. The process of claim 1, wherein the aqueous solution resulting from c) has a concentration of epihalohydrin and epihalohydrin hydrolysis products of less than 5 ppm.

20. The process of claim 17, wherein said epihalohydrin hydrolysis products are selected from the group consisting of 1,3-dichloro-2-propanol, 3-chloro-1,2-propanediol, 2,3-dichloro-1-propanol, and mixtures thereof.

21. The process of claim 1, wherein said at least one microorganism is present in a cell concentration greater than $5 \times 10^7$ cells/ml.

22. The process of claim 21, wherein said cell concentration is at least $10^8$ cells/ml.

23. The process of claim 22, wherein said cell concentration is at least $10^9$ cells/ml.

24. The process of claim 1, wherein the pH of b) is maintained for about 5 to about 50 minutes.

25. The process of claim 1, wherein said contacting of c) is for a period of time of from about 6 to about 50 hours.

26. The process of claim 1, further comprising d) deactivating or removing the enzymes or microbes, cooling to about 20° C. and stabilizing by adjusting the pH to a range of about 2.0 to about 5.0 by the addition of acid.

27. An additive for imparting improved wet strength to paper, produced by a process of claim 1.

28. A process for making an addictive for imparting wet strength to paper, said addictive comprising polyamine-epihalohydrin resin product having at least one of epihalohydrin or epihalohydrin hydrolyzates, the process comprising:

a) producing a polyamine-epihalohydrin polymer by reacting a polyamine selected from the group consisting of:

polyalkylene amine of the general formula $$H_2N((CH_2)_mNH)_n(CH_2)_mNH_2$$

where n is an interger from about 1 to about 6 and m is an integer from about 2 to about 8;

polyamidoamine of the general formula $$\{CO(CH_2)_yCONH(CH_2)_m(NH(CH_2)_nNH\}$$

where y is an integer from about 3 to about 5 and m and n have the same value as given above, and mixtures thereof, with epichlorohydrin in aqueous solution such that the epichlorohydrin used to make the polymer is in molar excess relative to secondary amine functionality in the polymine, and terminating the reaction, by cooling and adjusting the pH to less than 8.0;

b) adjusting the pH of the polyamine-epichlorohydrin solution to a range of from about 9.5 to about 10.5 and concurrently heating the solution to a range of from about 35 to about 50° C., and maintaining such conditions for about 5 to about 50 minutes;

c) contacting the aqueous solution resulting from the pH treatment of b) with at least one microorganism selected from the group consisting of *Arthrobacter histidinolovorans* NCIMB Registry No. 40274; *Arthrobacter erithii* NCIMB Registry No. 40271; *Agrobacterium tumefaciens* NCIMB Registry No. 40272; *Rhodococcus dehalogenans* NCIMB Registry No. 40383; *Pseudomonas cepacia* NCIMB Registry No. 40273, and mixtures thereof, at a cell concentration of greater than about $10^9$ cells/ml, or at least one enzyme isolated from said at least one microorganism, in an amount, and at a pH and temperature effective to dehalogenate residual quantities of organically bound halogen, at a pH in the range of from about 4 to about 8 and a temperature range of about 25 to about 35° C. for a period of time from about 6 to about 50 hours duration; and d) deactivating or removing the at least one microorganism or the at least one enzyme from the aqueous solution resulting from c), cooling to about 20° C. and stabilizing the resulting aqueous solution by adjusting the pH to a range of about 2.0 to about 5.0 by the addition of acid.

29. A process of making paper comprising:

a) producing a polyamine-epihalohydrin polymer in aqueous solution by reacting epihalohydrin with polyamine prepolymer, said epihalohydrin being in molar excess relative to the secondary amine functionality in the polyamine prepolymer;

b) concurrently heating and adjusting the pH of the polyamine-epihalohydrin resin in aqueous solution to a pH range of about 7.5 to 11 and temperature range effective to liberate halide ions from at least one of epihaloydrins and epihalohydrin hydrolyzates to solution, and maintaining said pH and temperature for at least 5 minutes; and c) contacting the aqueous solution resulting from b) with at least one microorganism, or at least one enzyme isolated from said at least one microorganism, in an amount, and at a pH and temperature effective to dehalogenate the aqueous solution; and d) adding the formulation resulting from c) to a stream in a papermaking process.

30. The process of claim 29, wherein said polyamine-epihalohydrin resin is prepared by reacting epihalohydrin and at least one member from the group consisting of:

polyalkylene amine of the general formula $$H_2N((CH_2)_mNH)_n(CH_2)_mNH_2$$

where n is an integer from about 1 to about 6 and m is an integer from about 2 to about 8; and polyamidoamine of the general formula $$\{CO(CH_2)_yCONH(CH_2)_m(NH(CH_2)_m)_nNH\}$$

where y is an integer from about 3 to about 5 and m and n have the same value as given above.

31. The process of claim 29, wherein said epihalohydrin is epichlorohydrin.

32. The process of claim 29, wherein a) is conducted under conditions wherein the ratio of epihalohydrin to secondary amine functionality is less than 3.5:1.

33. The process of claim 32, wherein a) is conducted under conditions wherein the ratio of epihalohydrin to secondary amine functionality is less than 1.9:1.

34. The process of claim 32, wherein a) is conducted under conditions wherein the ratio of epihalohydrin to secondary amine functionality is less than 1.5:1.

35. The process of claim 29, further comprising terminating said reaction a) by cooling, and said cooling is followed by adjusting the pH of said aqueous solution to less than 8.0.

36. The process of claim 29, wherein b) is conducted at a pH in the range of from about 8.0 to about 10.5.

37. The process of claim 36, wherein b) is conducted at a pH in the range of from about 9.5 to about 10.5.

38. The process of claim 29, wherein c) is conducted in the presence of a microorganism selected from the group consisting of *Arthrobacter histidinolovorans* NCIMB Registry No. 40274; *Arthrobacter erithii* NCIMB Registry No. 40271; *Agrobacterium tumefaciens* NCIMB Registry No. 40272; *Rhodococcus dehalogenans* NCIMB Registry No. 40383; *Pseudomonas cepacia* NCIMB Registry No. 40273, and mixtures thereof.

39. The process of claim 38, wherein c) is conducted in the presence of a microorganism selected the group consisting of *Arthrobacter histidinolovorans* HK1 and *Agrobacterium tumefaciens* HK7, and mixtures thereof.

40. The process of claim 38, wherein c) is conducted in the presence of a mixture comprising an excess of *Arthrobacter histidinolovorans* HK1 and 10 parts *Agrobacterium tumefaciens* HK7.

41. The process of claim 29, wherein the aqueous solution resulting from c) has a concentration of epihalohydrin and epihalohydrin hydrolysis products of less than 100 ppm.

42. The process of claim 29, wherein the aqueous solution resulting from c) has a concentration of epihalohydrin and epihalohydrin hydrolysis products of less than 10 ppm.

43. The process of claim 29, wherein the aqueous solution resulting from c) has a concentration of epihalohydrin and epihalohydrin hydrolysis products of less than 5 ppm.

44. The process of claim 43, wherein said epihalohydrin hydrolysis products are selected from the group consisting of 1,3-dichloro-2-propanol, 3-chloro-1,2-propanediol, 2,3-dichloro-1-propanol, and mixtures thereof.

45. The process of claim 29, wherein said cell concentration is at least $5 \times 10^7$ cells/ml.

46. The process of claim 29, wherein said cell concentration is at least $10^8$ cells/ml.

47. The process of claim 46, wherein said cell concentration is at least $10^9$ cells/ml.

48. The process of claim 1, wherein said polyamine-epihalohydrin resin is prepared in a) by producing a polyamine-epihalohydrin polymer by reacting polyamine prepolymer selected from the group consisting of:

polyalkylene amine of the general formula where n is an integer from about 1 to about 6 and m is an integer from about 2 to about 8;

polyamidoamine of the general formula where y is an integer from about 3 to about 5 and m and n have the same value as given above, and mixtures thereof,
with epichlorohydrin in aqueous solution such that the epichlorohydrin used to make the polymer is in molar excess relative to the secondary amine functionality in the polyamine prepolymer, and terminating the reaction, by cooling and adjusting the pH to less than about 8.0;

wherein said adjusting the pH of b) comprises adjusting the pH of the polyamine-epichlorohydrin resin in aqueous solution to a range of from about 9.5 to about 10.5 and concurrently heating the solution to a range of from about 35 to about 50° C., and maintaining such conditions for about 5 to about 50 minutes and the contacting of c) comprises contacting the aqueous solution resulting from the pH treatment of b) with microorganisms selected from the group consisting of *Arthrobacter histidinolovorans* NCIMB Registry No. 40274; *Arthrobacter erithii* NCIMB Registry No. 40271; *Agrobacterium tumefaciens* NCIMB Registry No. 40272; *Rhodococcus dehalogenans* NCIMB Registry No. 40383; *Pseudomonas cepacia* NCIMB Registry No. 40273, and mixtures thereof, at a cell concentration of greater than about $10^9$ cells/ml, or an enzyme, at a pH in the range of from about 4 to about 8 and a temperature range of about 25 to about 35° C. for a period of time from about 6 to about 50 hours duration; and d) deactivating or removing the enzymes or microbes resulting from c), cooling to about 20° C. and stabilizing by adjusting the pH to a range of about 2.0 to about 5.0.

49. The process of claim 48, wherein the aqueous solution resulting from c) has a concentratioin of epihalohydrin and epihalohydrin hydrolysis products of less than about 100 ppm.

50. The process of claim 48, wherein the aqueous solution resulting from c) has a concentration of epihalohydrin and epihalohydrin hydrolysis products of less than about 10 ppm.

51. The process of claim 48, wherein the aqueous solution resulting from c) has a concentration of epihalohydrin and epihalohydrin hydrolysis products of less than about 5 ppm.

* * * * *